(12) United States Patent
Schweizer

(10) Patent No.: US 10,474,328 B2
(45) Date of Patent: Nov. 12, 2019

(54) OPERATING ASSISTANT

(71) Applicant: SIEMENS HEALTHCARE GMBH, Erlangen (DE)

(72) Inventor: Hans Schweizer, Plattling (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/797,073

(22) Filed: Oct. 30, 2017

(65) Prior Publication Data

US 2018/0121041 A1 May 3, 2018

(30) Foreign Application Priority Data

Oct. 28, 2016 (DE) .................. 10 2016 221 252

(51) Int. Cl.
| | |
|---|---|
| G06F 3/0482 | (2013.01) |
| A61B 90/00 | (2016.01) |
| G06F 3/041 | (2006.01) |
| G06F 3/0488 | (2013.01) |
| G06F 19/00 | (2018.01) |
| G06F 9/451 | (2018.01) |

(52) U.S. Cl.
CPC ............ *G06F 3/0482* (2013.01); *A61B 90/37* (2016.02); *G06F 3/041* (2013.01); *G06F 3/0488* (2013.01); *G06F 9/453* (2018.02); *G06F 19/00* (2013.01)

(58) Field of Classification Search
None
See application file for complete search history.

(56) References Cited

U.S. PATENT DOCUMENTS

| | | | |
|---|---|---|---|
| 2011/0105190 A1* | 5/2011 | Cha ...................... | G06F 17/276 455/566 |
| 2016/0232896 A1* | 8/2016 | LeBeau .................. | G06F 3/167 |
| 2018/0081447 A1* | 3/2018 | Gummadi ............... | G06F 3/017 |

* cited by examiner

*Primary Examiner* — Kenneth B Lee, Jr.
(74) *Attorney, Agent, or Firm* — Laurence Greenberg; Werner Stemer; Ralph Locher

(57) ABSTRACT

An operating assistant controls device units and is configured such that elements of a selected functionality are clearly presented to the operator for selection in an operator-specific manner within an overview presentation. The elements are stored in a first or subsequent hierarchy level and further elements can likewise be depicted for selection on the visual display unit and selected operating functions and/or control functions can be executed.

12 Claims, 1 Drawing Sheet

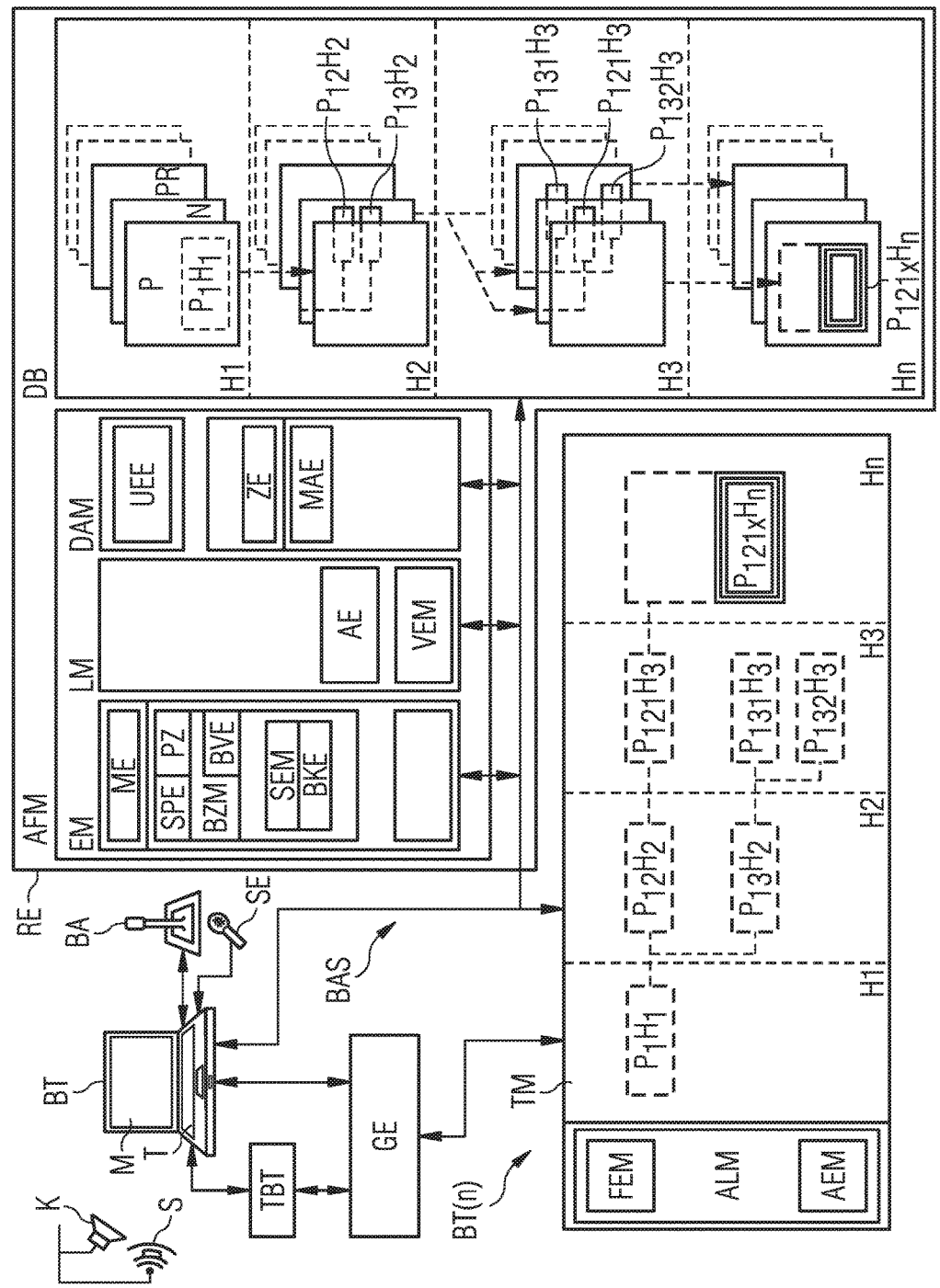

OPERATING ASSISTANT

CROSS-REFERENCE TO RELATED APPLICATION

This application claims the benefit, under 35 U.S.C. § 119, of German patent application DE 10 2016 221 252.4, filed Oct. 28, 2016; the prior application is herewith incorporated by reference in its entirety.

BACKGROUND OF THE INVENTION

Field of the Invention

Medical devices have many different functionalities which can be selected and triggered manually or electronically by a corresponding multiplicity of operating functions and/or control functions using control keys or operating elements in each case. This means that operating functions and/or control functions in hierarchically grouped menu structures can be invoked or selected and executed via touch screen-based input systems. Keys can be used to select corresponding operating functions and/or control functions or to open further menu options from which an operator can make a further selection from a multiplicity of operating functions and control functions. However, the selection of a specific operating function and/or control function in conjunction with a selection of stored parameters presupposes that the operator has a complete overview of the operating functions and/or control functions that can be selected in each case. In order to overcome this disadvantage, manufacturers offer overview help, e.g. online help, in which further explanations for different control functions can be retrieved by use of additional descriptions and/or hyperlinks.

U.S. patent publication No. 2016/0232896 describes an apparatus and a method for operating a user interface by voice input via a head-mountable device, such that the operator can depict a first or second menu on the head-mounted device.

SUMMARY OF THE INVENTION

The object of the invention is to specify an apparatus and a method for controlling a device unit, in particular a medical device unit, whereby the above cited disadvantage is overcome.

The subject matter of the invention is described as an operating assistant for storing, depicting, selecting and executing at least one operating function and/or control function to be assigned to a device unit. The operating assistant depicts at least one first element of an operating function and/or control function on a visual display unit, the element being stored in a first or subsequent hierarchy level. Further elements of the first element, from succeeding hierarchy levels and belonging to a selected operating function and/or control function, can likewise be depicted for selection on the visual display unit and selected operating functions and/or control functions can be executed.

The invention has the advantage that an operator is immediately shown an overview of the selected operating function and/or control function, from which a selection can be made without specific prior knowledge.

The invention has the advantage that an operator need not be familiar with the respective nested levels of hierarchically structured operating functions and/or control functions in order to properly select and/or initialize and execute required operating functions and/or control functions corresponding to an intended operating procedure.

The invention has the advantage that control functions from a lower or higher hierarchy level can be explicitly highlighted in a graphical user interface and/or on HW operating elements, and can therefore easily be recognized and/or selected by an operator.

The invention has the advantage that effective control of a device is provided without a lengthy familiarization phase for an operator.

The invention has the advantage that operating functions and/or control functions can be stored and retrieved in an operator-specific manner in an operating assistant.

The invention has the advantage that operating functions and/or control functions can be selected using voice control and, in the case of operating functions and/or control functions which are not safety-relevant, can be executed without confirmation of the operation and/or control.

The invention has the advantage that no functions can be directly triggered using the voice control.

In addition to the advantage that customer-specific keywords for operating functions and/or control functions can be stored or learned by the operating assistant, the invention has the further advantage that the operating functions and/or control functions incorporated therein can be retrieved immediately by the operator.

The invention has the advantage that separate confirmation by the operator is required in order to trigger safety-relevant operating functions and/or control functions in the device.

The invention has the advantage that the operating functions and/or control functions selected via voice control can be triggered manually.

The subject matter of the invention is explained in greater detail below with reference to a schematic illustration thereof.

The subject matter of the invention takes the form of an operating assistant for storing, depicting, selecting and executing at least one operating function and/or control function assigned to a device unit. For the purpose of controlling the multiplicity of operating functions and/or control functions of a medical device, at least one first element which can be stored in a first hierarchy level and is associated with at least one operating function and/or control function is provided, and can be depicted and selected on a visual display unit. Further elements in succeeding hierarchy levels, for more precise selection of the operating function and/or control function selected via the first element, can likewise be depicted on the visual display unit for selection. The totality of elements can therefore be depicted on the visual display unit as per the exemplary embodiment shown, subdivided into individual sections of an operating function and/or control function. By use of voice control, the individual elements of an operating function and/or control function can be invoked and verified and initialized for execution, wherein a safety-relevant operating function and/or or control function requires a separate confirmation for execution by the operator. In the exemplary embodiments described below, the individual elements of the operating functions and/or control functions can be selected using touch-sensitive icons depicted on at least one touch screen unit and, observing any applicable safety specifications, executed after actioning a key function or key sequence which can be specified. Entry points . . . , P1H1; P12H2, P13H2; . . . , . . . , . . . ; . . . , P121H3, P131H3 . . . ; . . . , P121xHn, . . . are associated or stored with these icons in each case, and respectively allow further elements of the operating function and/or control function to be invoked for presentation and operating functions and/or control functions to be selected for execution.

According to the subject matter of the invention, an operating assistant for operating and/or controlling device units is developed in such a way that operating functions and/or control functions assigned to a selected functionality, including configurable control parameters, are clearly presented to the operator for selection and/or offered for initialization and execution in an operator-specific manner within an overview presentation.

Other features which are considered as characteristic for the invention are set forth in the appended claims.

Although the invention is illustrated and described herein as embodied in an operating assistant, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The FIGURE of the drawing is an illustration of an operating assistant for a device or device unit to be controlled according to the invention.

DETAILED DESCRIPTION OF THE INVENTION

Referring now the single FIGURE of the drawing in detail there is shown an operating assistant BAS for a device or device unit to be controlled, in particular a medical device GE. The device GE, e.g. an x-ray device or a mobile C-arm, can be operated and/or controlled using an operating terminal BT and/or an input and/or control unit BE, for example. An input and/or control unit T, SE, BE may take the form of a joystick BE or a keypad T on a touch screen-based operator interface, for example. The elements depicted on the operating terminal BT, e.g. function fields of an operating function and/or control function, can be selected in this case via voice input SE, a keyboard T, a visual display unit such as touch screen-based terminal TBT or a touch screen monitor TM, and either further function fields are invoked or keypads depicted therein for elements or entry points of the operating functions and/or control functions are selected and/or triggered. The selection of elements or entry points from the function fields and/or the selection of a final operating function and/or control function can also be effected by voice capture, e.g. via a voice input unit SE. An operating function and/or control function is always triggered manually or via voice control or, in the case of safety-relevant operating functions and/or control functions, by voice input commands that are protected by safety circuits, possibly in combination with manual confirmation via mechanical or electronic switches on the device GE. The overview presentation shows a computing unit RE, which can be part of a control unit for the device GE that is to be controlled. Components of the computing unit RE include an assistant function module AFM and a database DB. The assistant function module AFM in turn has an input evaluation module EM, a learning module LM and a presentation module DAM. The database DB is so configured as to comprise a multiplicity of retrievable elements of operating functions and/or control functions and associated stored parameters, the elements being grouped together within a first, second, third and/or n-th hierarchy level H1, H2, H3, . . . , Hn. In the first hierarchy level H1, for example, elements of operating functions and/or control functions are grouped together or indicated under terms such as Processing P, Navigation N and Preparation PR. These elements can be selected via first or subsequent entry points PnH1. At least one first entry point XnH1 for basic functionalities of an imaging medical device in the clinical workflow is stored in the first hierarchy level H1 in this case. For example, the operating function and/or control function Preparation PR has an entry point PRnH1 to administration functions for patient management. These may include e.g. the capture of patient data such as name, date of birth, etc. or the selection of patients treated previously or the loading of their data including the relevant stored image data from a database. The operating function and/or control function Processing P, which belongs to the first hierarchy level H1, comprises e.g. functions for processing/modification image data of a registered patient, e.g. changing brightness parameters or magnifying/extracting specific image regions. The operating function and/or control function Navigation N contains at least a further first entry point NnH1, e.g. so that settings can be effected for externally connected image sources such as endoscopes or optical navigation systems. The functions of the first hierarchy level H1 are realized e.g. as different tabs or operating areas on a graphical user interface, such as those appearing as part of the "home page" after device startup, for example. Many of these functions assigned to the first hierarchy level H1 are allocated to succeeding hierarchy levels H2 to Hn, which allow access to settings that are in most cases increasingly specific as the hierarchy level or nesting level increases. This means that e.g. the elements of the operating function and/or control function Processing P offer a first entry point P1H1 in the first hierarchy level H1 and access to a multiplicity of possible image processing functions for image data that has been recorded or previously loaded. The second hierarchy level H2 in turn contains e.g. second entry points XnmH2 to further elements for operating functions and/or control functions for changing brightness and contrast by means of e.g. slide controls in a submenu of the second hierarchy level H2. The second hierarchy level H2 in turn contains second entry points PnmH2 to menu buttons or menu icons which are developed in the third hierarchy level H3. Therefore the third hierarchy level can also store accesses to submenus of the second hierarchy level H2, for example, so that parameters of so-called look-up tables for the brightness/contrast adjustment can be checked or an image inversion can be performed, for example. In the schematic illustration, the entry points are depicted to both the hierarchy levels H1, . . . , Hn in the database DB and on the touch screen monitor TM. If the operator wishes to process image data of a registered patient, they give a corresponding command to the operating assistant BAS via the voice input SE, e.g. "process image data of patient XY". All of the entry points P1H1; P12H2, P13H2; P121H3, P132H3; P132H3; P121xHn stored in the database are then clearly depicted on the touch screen monitor TM, e.g. with the corresponding hierarchy levels. By selecting one or more entry points P12H2, P121xHn, the operator can then have the desired processing step performed on the image data by the computer of the operating assistant, e.g. by means of voice recognition. The advantage of the invention is that when a first entry point P1H1, . . . , PR1H1 is selected the further operating elements and/or functionalities belonging to this entry point are clearly displayed to the operator. All of the functionalities that can be activated for a selected operating function and/or control function are displayed on the touch screen monitor/flat screen TM, e.g. with the respective hierarchy levels H1, ..., Hn. By means of a voice input or by simply tapping an icon belonging to the definition unit FEM, the operator defines the operating function and/or control function to be executed and triggers it by means of a voice input or e.g. by actioning the trigger unit AEM or by tapping the icon for a selected functionality which is marked graphically or in color on the touch screen monitor TM or specific operating element BE.

The input signals that can be input by a multiplicity of different input means T, TBT, TM, BT, BE, ..., SE are combined and converted into a nomenclature of the operating assistant BAS by an input evaluation module EM. Indicated as input means are, for example, an operating terminal BT featuring a keyboard T or a touchscreen monitor TBT, TM, a joystick BE or a voice input unit SE. Evaluation units for all manner of input units are provided in the input evaluation module EM. If the selection of the operating functions and/or control functions is effected by means of voice input, the acoustic signals captured by a voice input unit SE are forwarded to a voice recognition unit SPE, to be converted there into a machine language that can be processed by the operating assistant BAS. The converted acoustic voice inputs can be included in a configurable window on the monitor M, TBT, TM of the operating terminal BT for the operator as they are spoken. For the purpose of recognizing or processing the captured voice input, provision is made inter alia for a term assignment unit BZM, a term verification unit BVE, a semantics recognition unit SEM and a term clarification unit BKE. The voice recognition unit SPE can also be so designed as to recognize a language and/or a speaker. By means of a person recognition unit PZ, the operator who is speaking can be recognized on the basis of a stored voice profile. The operating assistant BAS also has a training unit AE or a presettings unit VEM, in particular a person-specific presettings unit VEM, in the learning module LM. By means of the training unit AE, operation-specific terms for operating functions and/or control functions can be assigned to a functionality stored in the database DB. Furthermore, the operator can optionally train the operating assistant BAS with further, customer-specific keywords relating to locally used customer-specific and special technical terms for specific functionalities, by speaking the term and then specifying to the system, in a special learning mode, which operating element/interactive means this term is to be associated with. The assignment is then stored in the database DB as an additional association possibility in an appropriate hierarchy level H1, ..., Hn with corresponding first, second or n-th entry points XnmH1, XnmH2, ..., Xnm ... Hn. If a plurality of possibilities exist for an assignment, the learning module LM asks the operator which function they want or offers the operator the most probable option for selection on the basis of invocation frequency. By means of the person-specific presettings unit VEM, work profiles can be assigned to specific persons and retrievably stored. The persons are understood to be patients, operators and person groups. The term assignment unit BZM is used to search for operating functions and/or control functions for the terms, which are likewise stored in the database DB. The database also has operating functions and/or control functions for which selectable or configurable parameter values can be set. If the request that is entered by means of voice input or via a keyboard cannot be assigned an executable operating function and/or control function from the database DB, the term verification unit BVE offers the operator similar terms for selection. If the operator is not able to find their formulated operating function and/or control function among these, they are given the option of transcribing the term they have cited. The transcribed term input by the operator or the operating function and/or control function to be executed is then forwarded to the semantics recognition unit SEM and the term clarification unit BKE in order to offer the operator further task-specific possibilities. The semantics recognition unit SEM is also designed in such a way that it can analyze complete queries and offer the operator solutions for these. If the desired operating function and/or control function is found, a corresponding overview presentation and/or a flow diagram is depicted, e.g. on a flat screen with touch screen function TM, by an overview generation unit UEE in the presentation module DAM. In this overview presentation, the operator can then select the operating function and/or control function and specify the required parameters by means of a definition unit FEM designed for this purpose. If the operator is sure they want a specific operating function and/or control function to be implemented in their device GE, they select a trigger unit for the selected functionality AEM, said trigger unit being assigned to a trigger module ALM. For example, the functionality AEM as part of the graphical user interface can actually be a button and/or a switching element or icon depicted on a touch screen operating element M, TBT, BE, or a dedicated additional operating element such as a separate hardware key or a foot pedal, for example. The schematic illustration of an operating assistant BAS according to the invention depicts a touch screen monitor unit TM with a possible example of voice-controlled selection for executing a selected functionality. The selection of a functionality can also take place using depictions on the monitor M of the operator terminal BT and an associated keyboard T. As explained above, an overview generation unit UEE is activated in parallel with the voice recognition and semantics analysis. By means of this overview generation unit UEE, according to the query and an assignment of selectable functionalities, possibly assigned to different hierarchy levels H1, ..., Hn, a graphical overview is generated on a monitor which is accessible to the operator. If a plurality of operating locations exist, the location of the operator can be detected in an assignment unit ZE using one or more optionally installed cameras K or sensors S in conjunction with directional microphones, and an input unit T, BT, TBT, TM, BE, ME can be assigned to the operator. By means of the schematically depicted touch screen monitor TM, the different operating functions and control functions of selected functionalities from different hierarchy levels H1, ..., Hn can then be displayed to the operator. By tapping on individual fields, possible further hierarchy levels can also be depicted and presented in a complete overview on the touch screen monitor. From the complete overview of possible operating functions and/or control functions and associated parameter values, the operator can then select the intended operating action or control action.

In the case of an operating input and/or function input which cannot yet be precisely identified for a desired operating function and/or control function, the operating assistant BAS makes it possible for the operator, e.g. by entering the word "prompt", to arrive at a specific functionality by means of further prompts from the system. Possible prompts include, for example:

"mirror image";
"I want to set the image contrast";

"export images";
"where can I register the patient?";
"I want to rotate the C-arm orbitally".

Working in the background of the operating assistant BAS, in addition to a voice recognition unit SPE which recognizes multiple languages, is the database DB described in the introduction, which assigns specific operating structures/elements to all possible keywords and sentence structures and depicts these on the touch screen monitor TM. In the case of a recognized keyword, the operating assistant BAS immediately opens the associated menu on an operating terminal BT or touch screen monitor TM which is accessible to the operator and where this function can be operated using a touch screen or mouse, for example. Tapping causes the fields on the touch screen monitor TM or relevant keyboards or operating buttons on the device units to be optically highlighted.

If a functionality is not integrated in an icon of an operating interface but is present on a joystick, for example, illuminated markings on the joystick light up and provide greater ease of use for the operator. If a plurality of operating locations exist, it is possible using one or more cameras K, optionally in conjunction with sensors S such as e.g. directional microphones, to detect the location of the person who wants to execute an operating function and/or control function on a device GE. In an assignment unit ZE assigned to the operating assistant BAS, the operating location which is determined as closest to the operator is highlighted, e.g. by signaling elements.

The following is a summary list of reference numerals and the corresponding structure used in the above description of the invention:
BAS Operating assistant
GE Device unit
SE Voice input unit
BT Operator terminal
M Monitor
T Keyboard
TBT Touch screen-based operating unit
BE Input/control unit
TM Touch screen A monitor/flat screen
K Camera
S Sensor
ZE Assignment unit
RE Computing unit
ALM Trigger module
FEM Definition unit
AEM Trigger unit for selected functionality
AFM Assistant functions module
EM Input evaluation module
SPE Voice recognition unit
PZ Person recognition unit
BZM Term assignment unit
BVE Term verification unit
SEM Semantics recognition unit
BKE Term clarification unit
LM Learning module
AE Training unit
VEM Person-specific presettings unit
DAM Presentation module
UEE Overview generation unit
ME Marking unit
DB Database
H1 First hierarchy level
XnH1 First entry points
P Processing
N Navigation
PR Preparation
H2 Second hierarchy level
XnmH2 Second entry points
H3 Third hierarchy level
Hn n-th hierarchy level
Xnm . . . Hn n-th entry points

The invention claimed is:

1. An operating assistant for selecting at least one operating function and/or control function assigned to a device unit, the operating assistant comprising:
a visual display unit; and
an overview generation unit for depicting at least one first element, which can be stored in a first hierarchy level and belongs to the operating function and/or the control function, on said visual display unit, and further elements of the first element from succeeding hierarchy levels and belonging to a selected operating function and/or a selected control function are depicted for selection likewise on said visual display unit and can be selected for execution; and
a learning module configured to recognize a first spoken term, to perform a first assignment between the recognized first spoken term and a first operating function and/or a control function, and to store the first assignment in a database after performing the first assignment;
said learning module configured to recognize a second spoken term, to perform a second assignment between the recognized second spoken term and a second operating function and/or a control function, and to store the second assignment in the database after performing the second assignment.

2. The operating assistant according to claim 1, wherein a selection of the first element and/or elements of the operating function and/or the control function is effected via voice input.

3. The operating assistant according to claim 1, wherein a selection of the first element and/or elements of the operating function and/or the control function is effected via a first entry point and/or further entry points.

4. The operating assistant according to claim 1, further comprising an input evaluation module which analyzes input signals.

5. The operating assistant according to claim 1, further comprising a presentation module for visual display of selected elements of the operating function and/or the control function.

6. The operating assistant according to claim 1, wherein further configurable parameters of the operating function and/or the control function are depicted in an overview presentation for selection on said visual display unit being a touchscreen monitor.

7. The operating assistant according to claim 1, further comprising a trigger unit configured for manual triggering of a selected operating function and/or selected control function.

8. The operating assistant according to claim 1,
further comprising a term assignment module assigned to the operating function and/or the control function; and
wherein the operating function and/or the control function is depicted on said visual display unit being a touchscreen monitor and/or operating element according to control structures, and further control options are presented according to a control command and are selected further by means of voice command according to a triggering functionality, and a selected control of a module of the device unit to be controlled can be triggered manually by an operator.

9. An operating assistant for selecting at least one operating function and/or control function assigned to a device unit, the operating assistant comprising:
- at least one first element which can be stored in a first hierarchy level and belongs to the operating function and/or the control function is depicted on a visual display unit, and that further elements of the first element from succeeding hierarchy levels and belonging to a selected operating function and/or a selected control function are depicted for selection likewise on the visual display unit and can be selected for execution, and
- a learning module configured to recognize a first spoken term, to perform a first assignment between the recognized first spoken term and a first operating function and/or a control function, and to store the first assignment in a database after performing the first assignment;
- said learning module configured to recognize a second spoken term, to perform a second assignment between the recognized second spoken term and a second operating function and/or a control function, and to store the second assignment in the database after performing the second assignment.

10. The operating assistant according to claim 9, further comprising at least one camera for detecting a location of a person wanting to execute the at least one operating function and/or control function.

11. The operating assistant according to claim 1, further comprising at least one camera for detecting a location of a person wanting to execute the at least one operating function and/or control function.

12. The operating assistant according to claim 1, wherein said visual display unit includes a display formed as a touchscreen.

* * * * *